(12) United States Patent
Takagi et al.

(10) Patent No.: US 8,809,360 B2
(45) Date of Patent: Aug. 19, 2014

(54) USE OF A PYRIDINE COMPOUND FOR THE PREPARATION OF A MEDICAMENT FOR THE TREATMENT OF SKIN LESIONS

(75) Inventors: Tamotsu Takagi, Osaka (JP); Atsuko Naotsuka, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 847 days.

(21) Appl. No.: 11/665,807

(22) PCT Filed: Oct. 28, 2005

(86) PCT No.: PCT/JP2005/020241
§ 371 (c)(1), (2), (4) Date: Apr. 19, 2007

(87) PCT Pub. No.: WO2006/046774
PCT Pub. Date: May 4, 2006

(65) Prior Publication Data
US 2009/0069307 A1    Mar. 12, 2009

(30) Foreign Application Priority Data
Oct. 29, 2004    (JP) .................................. 2004-315553

(51) Int. Cl.
| A61K 31/435 | (2006.01) |
| A61K 31/47 | (2006.01) |
| A61K 31/44 | (2006.01) |
| A61K 31/502 | (2006.01) |

(52) U.S. Cl.
USPC ........... 514/277; 514/312; 514/314; 514/307; 514/309; 514/248

(58) Field of Classification Search
None
See application file for complete search history.

(56) References Cited

U.S. PATENT DOCUMENTS

| 5,342,941 | A | 8/1994 | Iwasaki et al. |
| 5,965,730 | A | 10/1999 | Ukita et al. |
| 5,969,140 | A | 10/1999 | Ukita et al. |
| 6,005,106 | A | 12/1999 | Ukita et al. |
| 6,127,363 | A | 10/2000 | Doherty, Jr. et al. |
| 6,214,996 | B1 * | 4/2001 | Ukita et al. .................. 546/237 |
| 6,716,987 | B1 | 4/2004 | Ohshima et al. |
| 2002/0065286 | A1 | 5/2002 | Davies et al. |
| 2003/0195233 | A1 | 10/2003 | Magee |
| 2004/0038958 | A1 | 2/2004 | Rundfeldt et al. |
| 2004/0180900 | A1 * | 9/2004 | Takigawa et al. ........ 514/252.16 |
| 2004/0204418 | A1 | 10/2004 | Ukita et al. |
| 2005/0220791 | A1 | 10/2005 | Olmarker |

FOREIGN PATENT DOCUMENTS

| GB | 2 333 041 A | 7/1999 |
| JP | 2001-031679 | 6/2001 |
| JP | 2004-196785 | 7/2004 |
| WO | WO 03/068235 A1 | 8/2003 |
| WO | WO 03/073981 * | 9/2003 |
| WO | WO 2004/006920 | 1/2004 |
| WO | WO 2004/037183 A2 | 5/2004 |

OTHER PUBLICATIONS

Japanese Journal of Pharmacology (1995); vol. 67 (Suppl. I): p. 275 (P3-116).
Laure Favot et al., "VEGF-induced HUVEC migration and proliferation are decreased by PDE2 and PDE4 inhibitors," Thromb Haemost Aug. 2003, vol. 90, No. 2, pp. 334-343.
Robert D. Galiano et al., "Topical Vascular Endothelial Growth Factor Accelerates Diabetic Wound Healing through Increased Angiogenesis and by Mobilizing and Recruiting Bone Marrow-Derived Cells," American Journal of Pathology, vol. 164, No. 6, Jun. 2004, pp. 1935-1947.
Jianyuan Chai et al., "Serum response factor is a critical requirement for VEGF signaling in endothelial cells and VEGF-induced angiogenesis," The FASEB Journal, vol. 18, Aug. 2004, pp. 1264-1266.
Examination Report dated Dec. 9, 2008 issued in correspondhg European patent application.

(Continued)

*Primary Examiner* — Bong-Sook Baek
(74) *Attorney, Agent, or Firm* — Finnegan, Henderson, Farabow, Garrett & Dunner, L.L.P.

(57) ABSTRACT

The present invention relates to use of a pyridine compound of the following formula [I]: wherein R is a substituted pyridyl group having the following formula: $R^0$ is a $C_{1-6}$ alkoxy-$C_{1-6}$ alkyl group, $R^1$ and $R^2$ are the same or different and a $C_{1-6}$ alkoxy group, X is a group of the formula: =N— or a group of the formula: Ring A is a saturated or unsaturated 10-membered nitrogen-containing hetero-bicyclic group optionally having a substituent(s), the dotted line means the presence or absence of a double bond, or a pharmaceutically acceptable salt thereof for the preparation of a medicament for treatment of skin lesion.

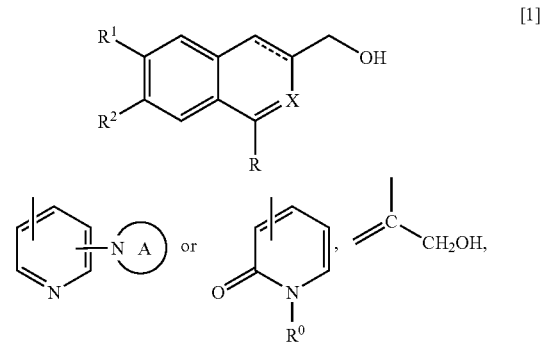

3 Claims, No Drawings

(56) References Cited

OTHER PUBLICATIONS

Griseldis Hübner et al, "Differential Regulation of Pro-Inflammatory Cytokines During Wound Healing in Normal and Clucocorticoid-Treated Mice," Cytokine, vol. 8, No. 7 (Jul. 1996), pp. 548-556.

Leif R. Lund et al., "Functional overlap between two classes of matrix-degrading proteases in wound healing," EMBO (European Molecular Biology Organization) Journal, vol. 18, No. 17, Sep. 1, 1999; pp. 4645-4656, ISSN: 0261-4189.

L. J. Zhou et al., "Stimulatory Effects of dibutyryl cyclic adenosine monophosphate on cytokine production by keratinocytes and fibroblasts," British Journal of Dermatology, vol. 143, No. 3, Sep. 2000, pp. 506-512, ISSN: 0007-0963.

International Preliminary Report on Patentability for PCT/JP2005/020241 dated May 1, 2007 (7 pages).

Iwasaki, Tameo et al., "Novel Selective PDE IV Inhibitors as Antiasthmatic Agents. Synthesis and Biological Activities of a Series of 1-Aryl-2,3-bis(hydroxymethyl)naphthalene Lignans," J. Med. Chem. 1996, 39, 2696-2704.

Souness, John E. et al., "Immunosuppressive and Anti-Inflammatory Effects of Cyclic AMP Phosphodiesterase (PDE) Type 4 Inhibitors," Immunopharmacology 47 (2000) 127-162.

JP Office Action for Corresponding JP Application No. 2005-313669 dated Jan. 17, 2012.

\* cited by examiner

USE OF A PYRIDINE COMPOUND FOR THE PREPARATION OF A MEDICAMENT FOR THE TREATMENT OF SKIN LESIONS

TECHNICAL FIELD

The present invention provides a novel use of a pyridine compound for the preparation of a medicament useful for the treatment of skin lesions such as wounds or skin ulcers. The present invention also provides a novel use of a pyridine compound for the preparation of an agent useful for promoting dermal microvascular endothelial cell-proliferation. The present invention further provides a method for treatment skin lesions which comprises administering the pyridine compound to a mammal in need of such treatment.

BACKGROUND ART

Various factors may cause skin lesions such as wounds, decubitus ulcer or thermal ulcer. Such skin lesions causing considerable patients' distress has been realized also as a pharmacoeconomically serious problem, because it often requires a long-term treatment to repair the skin lesion especially in case of chronic skin lesions such as decubitus ulcer.

The skin lesion healing is accomplished, in general, through a serial events comprising (1) inflammation phase, (2) cell-proliferation phase and (3) epidermis/corium-reconstitution phase. It is considered that various factors such as a platelet-derived growth factor (PDGF), a basic fibroblast growth factor (bFGF), a vascular endothelial cell growth factor (VEGF), keratinocyte growth factor (KGF), hepatocyte growth factor (HGF) and the like work under highly complicated relationships in the healing process. From a histopathological aspect, transient angiogenesis is an essential event in the process of skin lesion healing. In this regard, among the growth factors mentioned above, VEGF is one of primary promoting factors of angiogenesis and promote the skin lesion healing (*American Journal of Pathology* (2004): Vol. 164(6), pp 1935-47, *FASEB Journal* (2004): Vol. 18(11), pp 1264-66).

As an agent for the treatment of skin lesion, a prostaglandin $E_2$ preparation (alprostadil alphadex), dibutyryl cAMP preparation (bucladecin sodium), a sucrose/povidone iodide preparation, a tretinoin tocoferyl preparation and the like has been known. These agents, however, are not always efficient in treatment of chronic skin lesions such as chronic skin ulcers.

Recently, bFGF, one of the growth factors mentioned above, was developed owing to its physiological activity (angiogenesis-promoting activity) based on fibroblast-, vascular endothelial cell- and vascular smooth muscle cell-proliferation promoting activity and coming into practical use.

There are some other medicaments which may be used as an agent for promoting the skin lesion healing. For example, some literatures report that a prostaglandin $I_1$, ($PGI_1$) derivative showed a promoting activity on wound healing in animal models (*Japanese Journal of Pharmacology* (1995): Vol. 67 (Suppl. I), p 275 ($P_3$-116)) or that a phosphodiesterase 5 inhibitor such as syldenafil being clinically used for treatment of electile dysfunction may be expected to promote wound healing due to its vasodilating activity mediated by increase in intracellular cGMP level (WO2002/015893). However, these drugs are not coming into practical use yet.

On the other hand, there are some literatures to report that a certain kind of compounds, for example, an oxygen-containing heterocyclic compound such as a benzofuran compound (U.S. Pat. No. 6,716,987) or a nicotinic acid compound (US Patent Publication No. 2003/0195233) may be expected to show wound healing-promoting effect. However, neither their mechanism of action in wound healing process nor clinical usefulness remains to be proved.

Meanwhile, a pyridine compound (i.e., a pyridyl-substituted naphthalene compound and a pyridyl-substituted isoquinoline compound), which is an active ingredient of the present invention, has been known as an anti-asthma agent having a bronchoconstriction-inhibitory activity and airway inflammation-inhibitory activity mediated by its PDE4-inhibitory activity (EP748805, EP848000). But their skin lesion healing-promoting activity has never been reported.

DISCLOSURE OF INVENTION

The present invention relates to use of a pyridine compound of the following formula [I]:

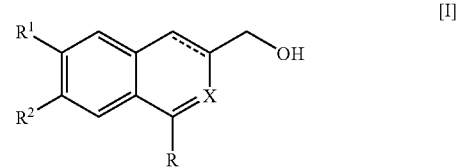

wherein R is a substituted pyridyl group having the following formula:

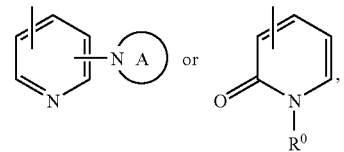

$R^0$ is a $C_{1-6}$ alkoxy-$C_{1-6}$ alkyl group, $R^1$ and $R^2$ are the same or different and a $C_{1-6}$ alkoxy group, X is a group of the formula: =N— or a group of the formula:

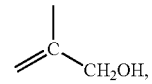

Ring A is a saturated or unsaturated 10-membered nitrogen-containing hetero-bicyclic group optionally having a substituent(s), and the dotted line means the presence or absence of a double bond, or a pharmaceutically acceptable salt thereof for the preparation of a medicament for treatment of skin lesion or for the preparation of an agent for promoting dermal microvascular endothelial cell-proliferation.

The medicament of the present invention is useful for promotion of healing of skin lesions such as wounds (traumatic wound, post-surgical wound and the like), decubitus ulcer, chronic skin ulcers (thermal ulcer, vascular obstructive ulcer including leg ulcer, diabetic ulcer and the like).

The precise mechanism of action of the compound [I] or a pharmaceutically acceptable salt thereof in the process of skin lesion-healing remains to be seen. Contemporarily, its potent promoting activity on dermal microvascular endothelial cell proliferation may lead to a possible hypothesis that a chain of responses comprising the increased expression of a vascular endothelial cell-specific mytogen (VEGF) induced by such pyridine compound and VEGF-induced cell migration and proliferation followed by promotion of angiogenesis in a target tissue plays an important role in skin lesion-healing, although other growth factors such as FGF induced by VEGF might be co-operatively involved in such process.

BEST MODE TO CARRY OUT INVENTION

Examples of the compound [I] as an active ingredient of the present invention include a compound in which R is a group of the formula:

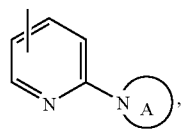

the 10-membered nitrogen-containing hetero-bicyclic group in the Ring A is a 10-membered nitrogen-containing hetero-bicyclic group optionally further containing a heteroatom(s) selected from nitrogen atom, oxygen atom and sulfur atom (said heterocyclic group may be partially or fully hydrogenated). Such heterocyclic group includes a quinolyl group, an isoquinolyl group, a quinazolinyl group, a phthalazinyl group, a naphthylidinyl group, a quinoxalinyl group and a benzothiazinyl group (said heterocyclic group may be partially or fully hydrogenated). The 10-membered hetero-bicyclic group may have one or more substituent(s). Such substituents include a group(s) selected from a hydroxyl group, an oxo group, a saturated or unsaturated 6-membered nitrogen-containing hetero-monocyclic group-substituted $C_{1-6}$ alkoxy group, di($C_{1-6}$ alkyl)phenyl group and a saturated or unsaturated 6-membered nitrogen-containing hetero-monocyclic group. In case that the substituent on the hetero-bicyclic group is or includes a saturated or unsaturated 6-membered nitrogen-containing hetero-monocyclic group, example of such heterocyclic group includes a pyridyl group, a dihydropyridyl group, a pyrimidinyl group, a morpholino group, a piperidinyl group and the like.

Among the substituted Ring A mentioned above, preferred examples of those Ring A include a 10-membered nitrogen-containing hetero-bicyclic group substituted by at least an oxo group and/or a hydroxyl group. Examples of such heterocyclic group include a group of the following formula:

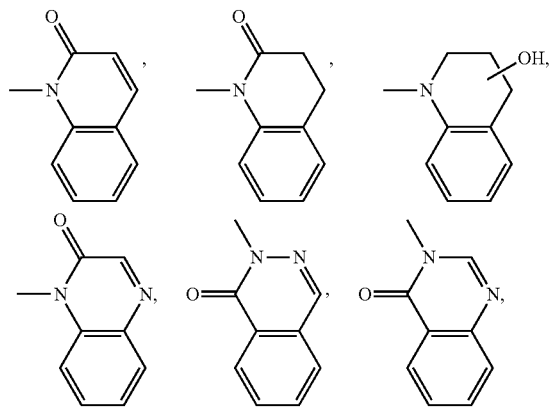

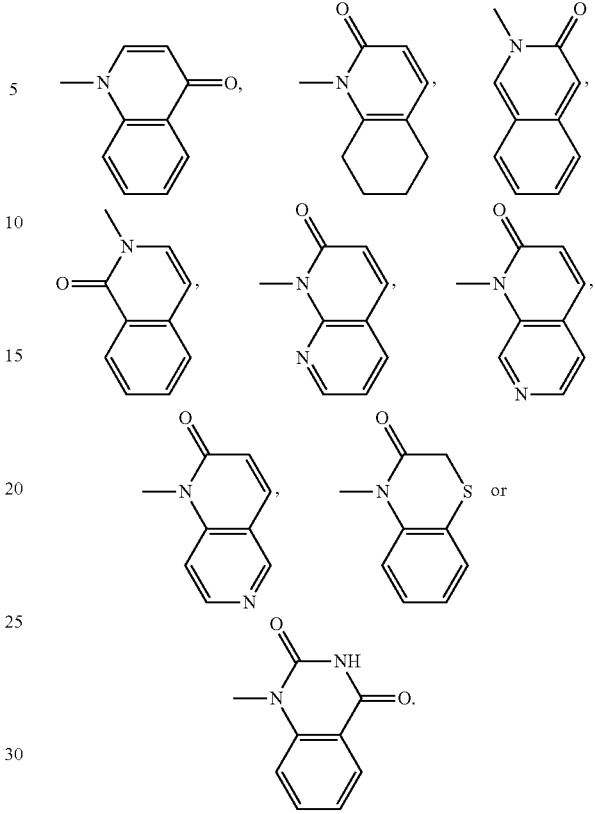

Meanwhile, said hetero-bicyclic group may further have a substituent(s) exemplified as above in addition to the oxo group and/or hydroxyl group.

More concretely, examples of the compound [I] as an active ingredient of the present invention is a compound of the following formula [I-A] or [I-B]:

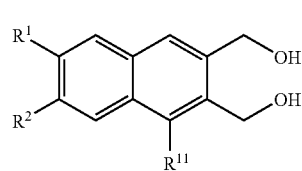

[I-A]

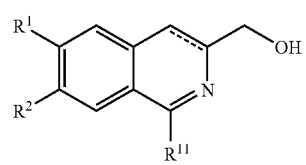

[I-B]

wherein $R^{11}$ is a group of the following formula:

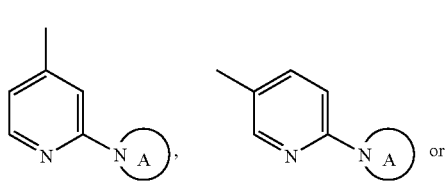

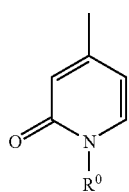

Ring A is (i) an oxo-substituted dihydro- or tetrahydro-quinolyl group optionally substituted by a group selected from a hydroxyl group and a pyridyl group, (ii) a hydroxy-substituted dihydro- or tetrahydro-quinolyl group, (iii) an oxo-substituted hexahydro-quinolyl group optionally substituted by a hydroxyl group, (iv) an oxo-substituted dihydro- or tetrahydro-isoquinolyl group optionally substituted by a group selected from a hydroxyl group, a morpholino-$C_{1-6}$ alkoxy group, a pyridyl-$C_{1-6}$ alkoxy group, a piperidinyl-$C_{1-6}$ alkoxy group and a morpholino group, (v) an oxo-substituted dihydro- or tetrahydro-phthalazinyl group optionally substituted by a group selected from a hydroxyl group, a di($C_{1-6}$ alkyl)aminophenyl group, a pyridyl group and a pyrimidinyl group, (vi) an oxo-substituted dihydro- or tetrahydro-quinazolinyl group optionally substituted by a hydroxyl group, (vii) an oxo-substituted dihydro- or tetrahydro-quinoxalinyl group optionally substituted by a hydroxyl group or (viii) an oxo-substituted dihydro- or tetrahydro-naphthylidinyl group optionally substituted by a hydroxyl group, and $R^1$ and $R^2$ are the same or different and a $C_{1-6}$ alkoxy group or a pharmaceutically acceptable salt thereof.

Another concrete examples of the compound [I] as an active ingredient of the present invention include a compound [I] in which R is a 2-oxo-1-substituted pyridin-4-yl group of the formula:

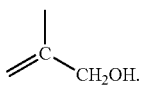

and X is a group of the formula:

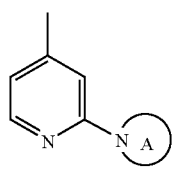

Among them, more concrete examples include a compound in which $R^0$ is methoxymethyl group and $R^1$ and $R^2$ are ethoxy group.

Among the pyridine compounds [I] mentioned above, examples of a pharmacologically preferable compound include a compound [I-A] or [I-B] in which $R^{11}$ is a 2-substituted pyridin-4-yl group of the formula:

and $R^1$ and $R^2$ are the same or different and methoxy group or ethoxy group.

Among the compounds mentioned above, examples of a more pharmacologically preferable compound include a compound [I-A] or [I-B] in which the Ring A in $R^{11}$ is (a) a hydroxy-substituted dihydro- or tetrahydro-quinolyl group, (b) an oxo-substituted dihydro- or tetrahydro-isoquinolyl group substituted by a group selected from a pyridyl-substituted $C_{1-6}$ alkoxy group and a morpholino-$C_{1-6}$ alkoxy group, (c) an oxo-substituted dihydro- or tetrahydro-phthalazinyl group substituted by a group selected from a pyridyl group, a pyrimidinyl group and a di($C_{1-6}$ alkyl)aminophenyl group or (d) an oxo-substituted dihydro- or tetrahydro-quinazolinyl group.

Among them, examples of a further pharmacologically preferable compound include a compound [I-A] or [I-B] in which the Ring A is a group of the following formula:

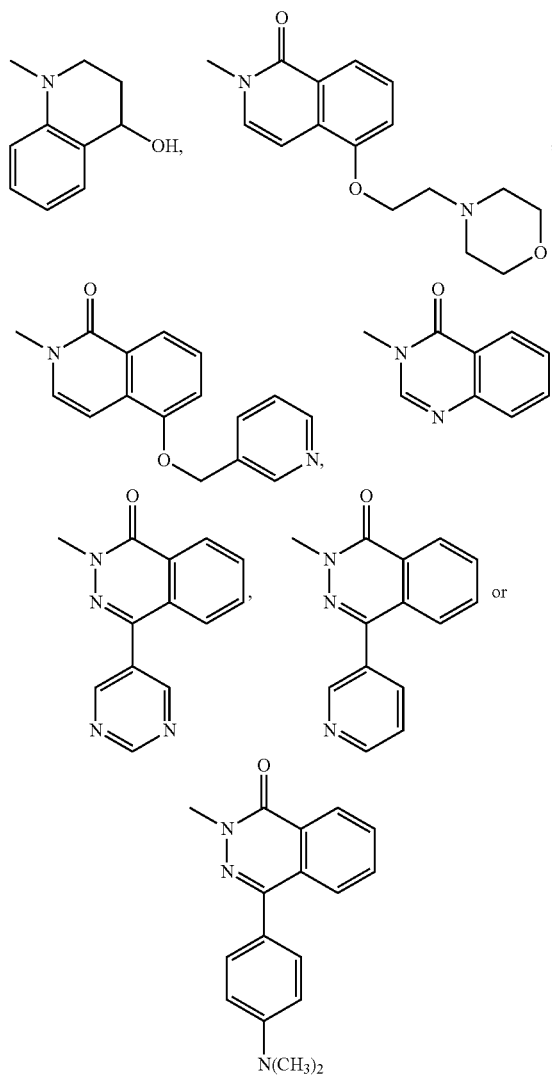

Among them, examples of a particularly pharmacologically preferable compound include a compound selected from the group consisting of: 2-(4-hydroxy-1,2,3,4-tetrahydroquinolin-1-yl)-4-[2,3-bis(hydroxymethyl)-6,7-dimethoxynaphthalen-1-yl]pyridine; 4-[2,3-bis(hydroxymethyl)-6,7-dimethoxynaphthalen-1-yl]-2-[1-oxo-1,2-dihydro-5-(2- morpholinoethoxy)-isoquinolin-2-yl]pyridine; 4-[2,3-bis (hydroxymethyl)-6,7-dimethoxynaphthalen-1-yl]-2-[1-oxo-1,2-dihydro-5-(3-pyridylmethoxy)-1-isoquinolin-2-yl] pyridine; 4-(3-hydroxymethyl-6,7-dimethoxyisoquinolin-1-yl)-2-[4-(3-pyridyl)phthalazin-1(2H)-one-2-yl]pyridine; and 4-[(3S)-3-hydroxymethyl-3,4-dihydro-6,7-dimethoxyisoquinolin-1-yl]-2-[1-oxo-5-(3-pyridylmethoxy)-1,2-dihydroisoquinolin-2-yl]pyridine; or a pharmaceutically acceptable salt thereof.

When the compound [I] of the present invention has an asymmetric carbon atom(s) in its molecule (e.g., in the dihydroisoquinoline moiety or the Ring A), it may exist in the form of a stereoisomer thereof (diastereoisomers, optical isomers) owing to said asymmetric carbon atom(s) thereof, and the present invention also includes either one of the stereoisomers and a mixture thereof.

The medicament of the present invention is useful for promotion of healing of skin lesions such as wounds (traumatic wound, post-surgical wound and the like), decubitus ulcer, chronic skin ulcers (thermal ulcer, vascular obstructive ulcer including leg ulcer, diabetic ulcer and the like).

Examples of the pharmaceutically acceptable salt of the compound [I] include an inorganic acid salt such as a hydrochloride, a sulfate or a hydrobromide, and an organic acid salt such as an acetate, fumarate, an oxalate, a methanesulfonate or a maleate.

The compound [I] or a pharmaceutically acceptable salt thereof can be prepared by a known process as described in, for example, EP748805B1, EP848000B1 or U.S. Pat. No. 5,342,941.

The compound [I] or a pharmaceutically acceptable salt thereof can be administered topically onto the lesion site directly or indirectly and its dose may vary in accordance with the ages, weights and conditions of the subject/patients in need of the treatment of skin lesion, or the kind or degree of such skin lesion. For example, it is usually in the range of about 0.05 to 100 mg/skin lesion, preferably 0.1 to 10 mg/skin lesion. The dosing frequency can be determined appropriately as required. For example, it is usual to administer once to four times daily, preferably once to twice daily.

The medicament for the treatment of skin lesion of the present invention has a potent promoting activity on dermal microvascular cell proliferation and can be thereby applicable to the treatment (e.g., promotion of healing) of skin lesions such as wounds (traumatic wound, post-surgical wound and the like), decubitus ulcer or chronic skin ulcers (thermal ulcer, vascular obstructive ulcer including leg ulcer, diabetic ulcer and the like).

Moreover, the compounds [I] as an active ingredient of the present invention include a compound which does not exhibit substantially a certain undesired effect such as cytotoxicity, photosensitivity and the like at least within the range of effective dose for the treatment of skin lesion. The medicament for the treatment of skin lesion of the present invention comprising such compound may be useful as a therapeutic agent from an aspect of safety.

In addition to the compound [I] or a pharmaceutically acceptable salt thereof as an active ingredient, one or more pharmaceutically acceptable additive(s) such as a penetration enhancer, a pH-adjusting agent, a preservative, a flavoring agent, a dispersing agent, a humectant, a stabilizing agent, an antiseptic agent, a suspending agent or a surfactant can be incorporated into the medicament of the present invention, if required.

Examples of the penetration enhancer include a monovalent alcohol having 20 carbon atoms or less than 20 carbon atoms such as ethyl alcohol, isopropyl alcohol and stearyl alcohol, a pyrrolidone compound such as 2-pyrrolidone and 1-methyl-2-pyrrolidone, a urea compound such as urea and thiourea, a cyclodextrine compound such as alpha-dextrine, menthol, 1-dodecylazacyclohepthan-2-one, calcium thioglycolate, limonene and the like. The incorporation amount of said penetration enhancer may vary in accordance with the form of preparation or the carrier base. It is usually in the range of 0.1 w/w % or greater, preferably 0.3 w/w % or greater from a viewpoint of effectively expressing the penetration-enhancing activity, and in the range of 10 w/w % or less, preferably 5 w/w % or less from a viewpoint of suppressing adverse drug reactions.

The pH-adjusting agent may be an inorganic acid such as hydrochloric acid, sulfuric acid or phosphoric acid and an organic acid such as acetic acid, succinic acid or malic acid or a metal salt thereof. The incorporation amount of said pH-adjusting agent may vary in accordance with the form of the preparation or the carrier base. It is usually in the range so that the pH of the objective composition is within the range from 4 to 8.

The preservative may be paraben, methylparaben, chlorobuthanol, benzyl alcohol and the like.

The flavoring agent may be menthol, rose oil, eucalyptus oil, d-camphor and the like.

The dispersing agent may be sodium methaphosphate, potassium polyphosphate, anhydrous silicic acid.

The humectant may be a propylene glycol, glycerin, sorbitol, sodium lactate, sodium hyaluronate and the like.

The stabilizing agent may be sodium sulfite, tocopherol, ethylenediaminetetraacetic acid (EDTA), citric acid and the like.

The suspending agent may be a powdered tragacanth, a powdered acacia, a bentonite, a carboxymethylcellulose and the like.

The surfactant may be a polyoxyethylenehydrogenated castor oil, a sorbitan fatty acid ester such as sorbitan sesquioleate, a polyoxyl stearate and the like.

The medicament for the treatment of skin lesion of the present invention can be used as a topical agent for administering directly onto the lesion/wound site in the form of ointments, creams, lotions, liniments, cataplasms, plasters, patches, gels, solutions and the like.

For the ointments or creams mentioned above, an oily base or an emulsion base can be used. The oily base may be a hydrocarbons such as a $C_{12-32}$-hydrocarbon including liquid paraffin, white petrolatum, squalen, squalan, plastibase and the like, a higher alcohol such as a monovalent $C_{12-30}$-aliphatic alcohol including lauryl alcohol, cetyl alcohol, stearyl alcohol, oleyl alcohol and the like, a higher fatty acid such as a saturated or unsaturated $C_{6-32}$-fatty acid including palmitic acid and stearic acid, a higher fatty acid ester such as myristyl palmitate, stearyl stearate, a fatty acid ester with a monovalent $C_{14-32}$-aliphatic alcohol including lanorine and carnauba wax, an ester of a saturated or unsaturated $C_{10-22}$-aliphatic acid with glycerine including glyceryl monolaurate or hydrogenated derivative thereof, a glycol compound including ethylene glycol, propylene glycol and polyethylene glycol, a vegetable oil and an animal oil.

The emulsion base may be an oil in water base, a water in oil base or a suspension base. Examples of the oil in water base include a base prepared by emulsifying or dispersing an oily ingredient such as lanolin, propylene glycol, stearyl alcohol, petrolatum, silicon oil, liquid paraffin, glyceryl monostearate, polyethylene glycol and the like with water in the presence or absence of a surfactant. Examples of the water in oil base include a base prepared by mixing an oily ingredient such as white petrolatum, liquid paraffin and the like with water in the presence or absence of a surfactant and then emulsifying or dispersing the mixture. The suspension base may be an aqueous base in the form of a gel prepared by mixing a suspending agent such as a starch, glycerin, a high viscosity carboxymethylcellulose, a carboxyvinyl polymer and the like with water.

The medicament for the treatment of skin lesion of the present invention can be prepared in the conventional manner to produce a topical preparation by, for example, mixing, emulsifying or suspending materials for a base, blending the active ingredient and other additives with the base and mixing them in a mixer such as a screw mixer.

The medicament for the treatment of skin lesion of the present invention can be used in any form of a suspension-, an emulsion- or a solution-type lotion. Examples of the base for a suspension type-lotion include a mixture comprising a suspending agent such as gums including acacia and tragacanth, cellulose compounds including methylcellulose and hydroxyethylcellulose, clays including bentonite and water. Examples of the base for an emulsion type-lotion include an emulsion comprising water and an oil such as fatty acids including stearic acid and oleic acid or higher aliphatic alcohols including cetyl alcohol. Examples of the base for a solution type-lotion include water and alcohols such as ethyl alcohol, glycerin or propylene glycol. Such lotions can be prepared by mixing the base and water, stirring the mixture, mixing the active ingredient and appropriate additives thereto and, if necessary filtering such mixture.

Examples of the base for a liniment include vegetable oils such as olive oil, alcohols such as ethyl alcohol or isopropyl alcohol and a mixture of such oils with water. Said liniment can be prepared by dissolving the active ingredient and if required mixing appropriate additives with the mixture.

Examples of the base for a cataplasm include water-soluble polymers such as a polyacrylic acid, a polyvinyl alcohol or a polyvinyl pyrrolidone. Said cataplasm can be prepared by mixing the active ingredient, the base and appropriate additives, heating followed by cooling the mixture.

Examples of the base for plasters or patches include a combination of carrier such as non-woven fabric, elastomers such as natural rubber or isoprene rubber, fillers such as zinc white or titanium oxide, adhering agents such as terpene resins, peeling agents such as vinyl acetate, softeners such as liquid paraffin or antioxidants such as dibutylhydroxytoluene (BHT). Said plasters and patches can be prepared by conventional manners such as a solution method and the like.

Examples of the solvent for a solution include water, ethyl alcohol, isopropyl alcohol, benzyl alcohol, polyethylene glycol such as PEG400, propylene glycol, propylene carbonate and a mixture thereof. Said solutions can be incorporated into gauze or dressings.

The incorporated amount of the active ingredient may vary in accordance with the form of preparations and could be 0.0025 to 5 w/w %, preferably 0.005 to 0.5 W/w % for the ointment and 0.1 to 200 mg/ml, preferably 0.1 to 20 mg/mL for the solution.

The medicament for the treatment of skin lesion of the present invention may also be used concomitantly with other agents for the treatment of wound or skin ulcer. Moreover, other physiologically active substances having an ability of promoting skin lesion/wound-healing (e.g., growth factors such as PDGF, TGF-α, TGF-β, bFGF, EGF and the like) may be, if required, incorporated into the pharmaceutical preparation of the present invention.

The present invention is illustrated in more detail by the following examples/experiments, but should not be construed to be limited thereto. The following compounds as shown in Table 1 (No. 1 to 11) are included within the extent of the compound [I] as an active ingredient of the present invention. Meanwhile, among the compounds in the Table 1, each compound having an asymmetric carbon atom(s) is that in the form of a racemic mixture, unless any representation of an optical isomer is described.

TABLE 1

(No. 1)

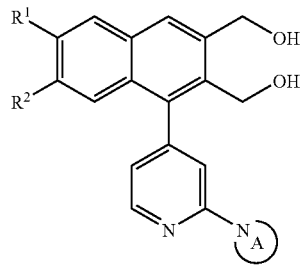

| Compound No. | $R^1$ | $R^2$ | Ring A |
|---|---|---|---|
| 1 | $C_2H_5O-$ | $C_2H_5O-$ | |

TABLE 1-continued

| | | | |
|---|---|---|---|
| 2* | CH₃O— | CH₃O— | (1-methyl-2-oxo-1,2-dihydroquinolin-4-yl)pyridine structure |
| 3 | CH₃O— | CH₃O— | 1-methyl-1,2,3,4-tetrahydroquinolin-4-ol structure |
| 4* | CH₃O— | CH₃O— | 2-methyl-5-(2-morpholinoethoxy)isoquinolin-1(2H)-one structure |
| 5* | CH₃O— | CH₃O— | 2-methyl-5-(pyridin-3-ylmethoxy)isoquinolin-1(2H)-one structure |
| 6 | CH₃O— | CH₃O— | 1-methyl-3,4-dihydroquinolin-2(1H)-one structure |

(No. 2)

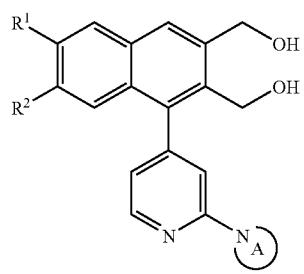

| Compound No. | R¹ | R² | Ring A |
|---|---|---|---|
| 7 | CH₃O— | CH₃O— | 1-methylquinolin-4(1H)-one structure |

TABLE 1-continued

| | | | |
|---|---|---|---|
| 8 | CH₃O— | CH₃O— | 2-methylphthalazin-1(2H)-one |
| 9* | CH₃O— | CH₃O— | 3-methyl-4-(pyridin-3-yl)phthalazin-1(2H)-one |
| 10* | CH₃O— | CH₃O— | 3-methyl-4-(pyrimidin-5-yl)phthalazin-1(2H)-one |
| 11* | CH₃O— | CH₃O— | 3-methyl-4-(pyridin-2-yl)phthalazin-1(2H)-one |
| 12* | CH₃O— | CH₃O— | 3-methyl-4-(pyridin-4-yl)phthalazin-1(2H)-one |
| 13* | CH₃O— | CH₃O— | 3-methylquinazolin-4(3H)-one |
| 14 | C₂H₅O— | CH₃O— | 3-methyl-4-(pyridin-3-yl)phthalazin-1(2H)-one |

TABLE 1-continued
(No. 3)
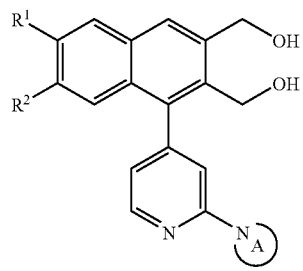
| Compound No. | R¹ | R² | Ring A |
|---|---|---|---|
| 15 | CH₃O— | CH₃O— | 2-methylisoquinolin-1(2H)-one |
| 16 | CH₃O— | CH₃O— | 1-methylquinolin-2(1H)-one |
| 17 | C₂H₅O— | C₂H₅O— | 1-methylquinolin-2(1H)-one |
| 18 | CH₃O— | CH₃O— | 1-methyl-5,6,7,8-tetrahydroquinolin-2(1H)-one |
| 19 | CH₃O— | CH₃O— | 2-methylisoquinolin-3(2H)-one |
| 20 | CH₃O— | CH₃O— | 4-hydroxy-1-methylquinolin-2(1H)-one |
| 21 | CH₃O— | CH₃O— | 5-hydroxy-2-methylisoquinolin-1(2H)-one |

TABLE 1-continued
(No. 4)
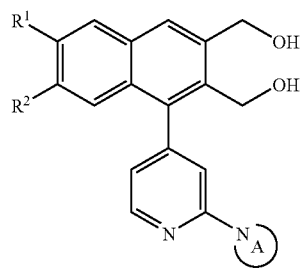
| Compound No. | R¹ | R² | Ring A |
|---|---|---|---|
| 22* | CH₃O— | CH₃O— | 2-methyl-1,2,3,4-tetrahydroisoquinolin-yl |
| 23* | CH₃O— | C₂H₅O— | 3-methyl-4-(pyridin-3-yl)phthalazin-1(2H)-one |
| 23B* | C₂H₅O— | CH₃O— | 3-methyl-4-(pyridin-3-yl)phthalazin-1(2H)-one |
| 24* | C₂H₅O— | C₂H₅O— | 3-methyl-4-(pyridin-3-yl)phthalazin-1(2H)-one |
| 25* | CH₃O— | CH₃O— | 4-(4-(dimethylamino)phenyl)-3-methylphthalazin-1(2H)-one |
| 26 | CH₃O— | CH₃O— | 2-methyl-4-hydroxyphthalazin-1(2H)-one |

TABLE 1-continued

| | | | |
|---|---|---|---|
| 27* | (CH₃)₂CHO— | CH₃O— | (structure: 1-(pyridin-3-yl)-3-methylphthalazin-4(3H)-one) |
| 28* | (CH₃(CH₂)₃O— | CH₃O— | (structure: 1-(pyridin-3-yl)-3-methylphthalazin-4(3H)-one) |

(No. 5)

[Structure: naphthalene core with R¹ and R² substituents on one ring, two CH₂OH groups, connected to a pyridine bearing N–Ring A]

| Compound No. | R¹ | R² | Ring A |
|---|---|---|---|
| 29 | CH₃O— | CH₃O— | 1-methylquinoxalin-2(1H)-one |
| 30* | CH₃O— | CH₃O— | 2-methyl-3-morpholinoisoquinolin-1(2H)-one |
| 31* | CH₃O— | CH₃O— | 2-methyl-5-(2-(piperidin-1-yl)ethoxy)isoquinolin-1(2H)-one |
| 32 | CH₃O— | CH₃O— | 1-methyl-1,8-naphthyridin-2(1H)-one |
| 33 | CH₃O— | CH₃O— | 1-methyl-1,6-naphthyridin-2(1H)-one |

TABLE 1-continued
| | | | |
|---|---|---|---|
| 34 | CH₃O— | CH₃O— | 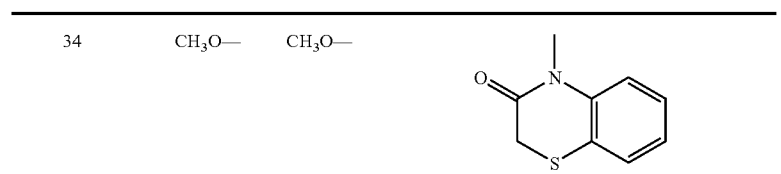 |
(No. 6)
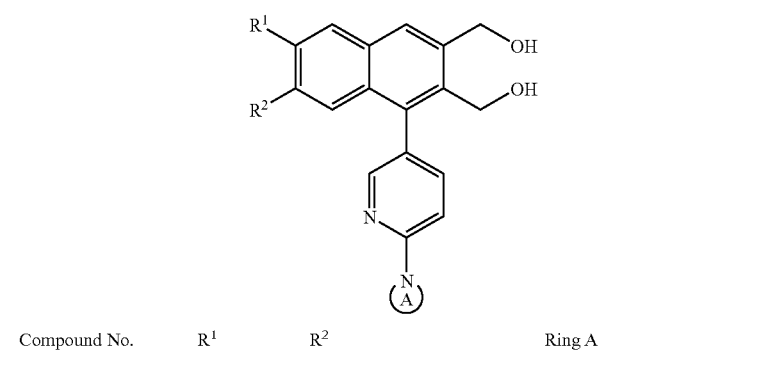
| Compound No. | R¹ | R² | Ring A |
|---|---|---|---|
| 35* | CH₃O— | CH₃O— | 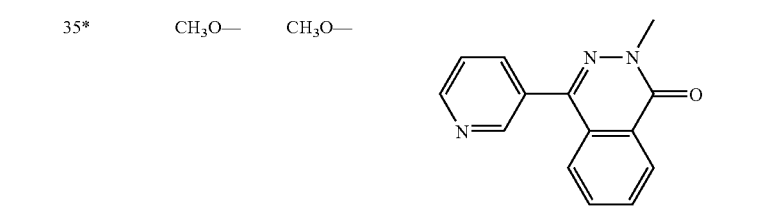 |
| 36 | CH₃O— | CH₃O— | 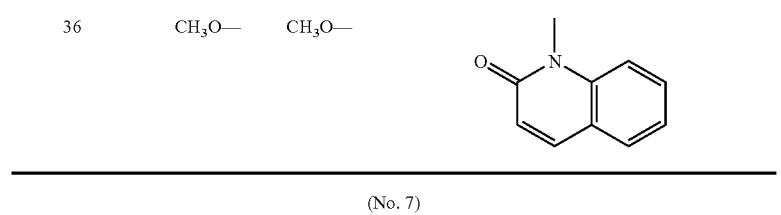 |
(No. 7)
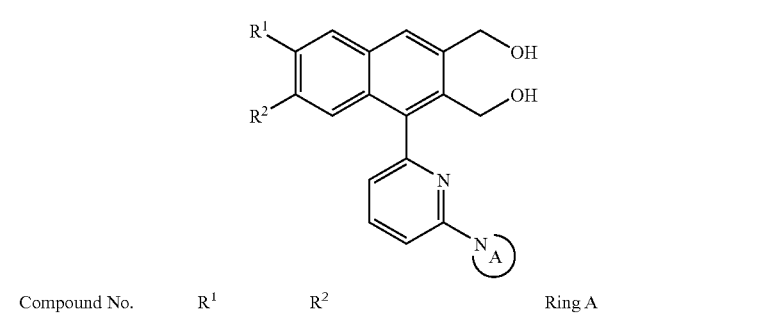
| Compound No. | R¹ | R² | Ring A |
|---|---|---|---|
| 37 | CH₃O— | CH₃O— | 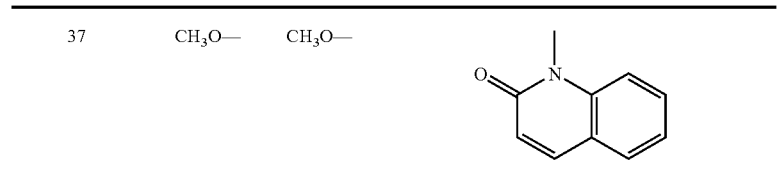 |

TABLE 1-continued
(No. 8)
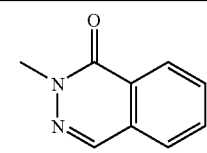
| Compound No. | R¹ | R² | Ring A |
|---|---|---|---|
| 38 | CH₃O— | CH₃O— | 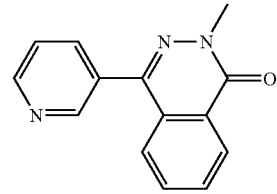 |
| 39* | CH₃O— | CH₃O— | 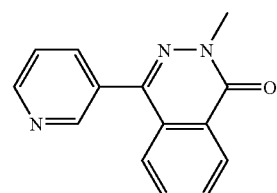 |
| 40* | C₂H₅O— | C₂H₅O— | 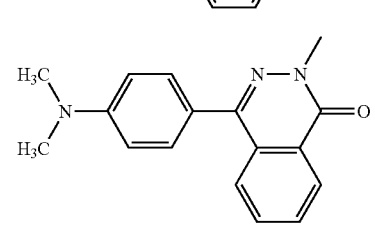 |
| 41 | CH₃O— | CH₃O— | |
(No. 9)
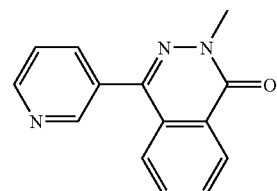
| Compound No. | R¹ | R² | Ring A |
|---|---|---|---|
| 42* | CH₃O— | CH₃O— | |

TABLE 1-continued
| 43* | CH₃O— | CH₃O— | 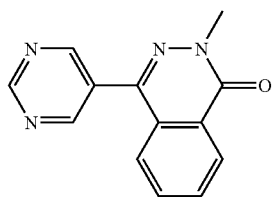 |
| 44* | CH₃O— | CH₃O— | 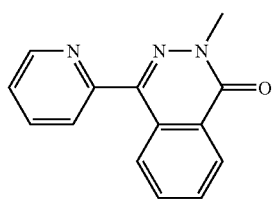 |
| 45* | CH₃O— | CH₃O— | 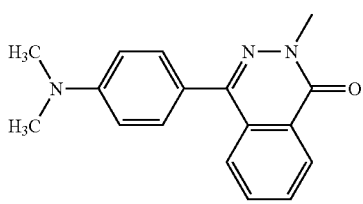 |
| 46* | CH₃O— | CH₃O— | 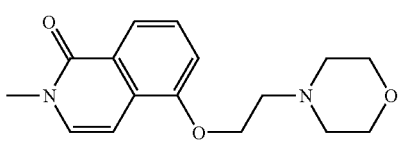 |
| 47* | CH₃O— | CH₃O— | 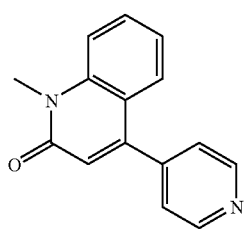 |
| 48* | CH₃O— | CH₃O— | 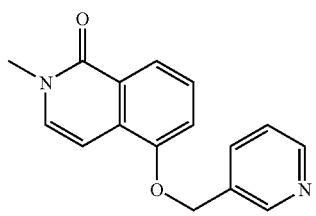 |
(No. 10)
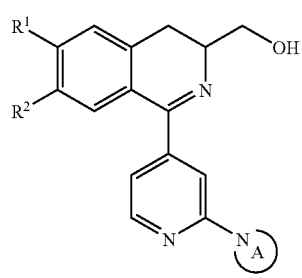

TABLE 1-continued

| Compound No. | R¹ | R² | Ring A |
|---|---|---|---|
| 49* | $C_2H_5O-$ | $C_2H_5O-$ | |
| 50* | $C_2H_5O-$ | $C_2H_5O-$ | |
| 51* | $C_2H_5O-$ | $C_2H_5O-$ | |
| 52* | $CH_3O-$ | $CH_3O-$ | |

(No. 11)

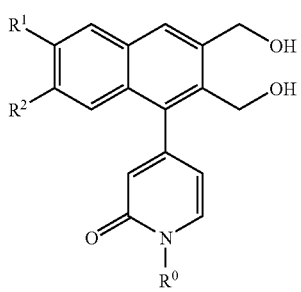

| Compound No. | R¹ | R² | R⁰ |
|---|---|---|---|
| 53 | $C_2H_5O-$ | $C_2H_5O-$ | $-(CH_2)_2OCH_3$ |

*hydrochloride

The present invention are illustrated in more detail by the following Experiments but should not be construed to be limited thereto.

EXPERIMENT 1

Promoting Activity In Vitro of the Pyridine Compound on Human Dermal Microvascular Endothelial Cell (HDMEC) Proliferation Method:

The wound healing-promoting activity of test compounds were investigated in terms of the promotion activity on HDMEC proliferation in the following manner. As a HDMEC, normal adult dermal microvascular endothelial cells (Hybridoma (1996): Vol. 15 (4), pp 279-288) were used in this study.

A suspension of HDMEC mentioned above ($2\times10^4$ cells/mL; Cryo HMVEC-Ad; trademark registered by Cambrex Inc.) were seeded on 48-well plate (250 µL/well). The cells were cultured in a proliferation medium (BletKit EGM-2-MV; trademark registered by Cambrex Inc.) for one day. After substituting an assay medium (450 µL, bFGF-, EGF- and VEGF-free BletKit EGM-2-MV; trademark registered by Cambrex Inc.) for the proliferation medium, a dimethylsulfoxide solution of the test compound (0.1 v/v %, 50 µL) was added to each well and the cells were cultured for 96 hours. After culturing, the assay medium was removed by aspiration and the residual cells were suspended in Isoton II solution (500 µL; Beckmann-Coulter Ltd.) containing 0.05% trypsin and 0.02% ethylenediaminetetraacetic acid. The suspension was diluted (11-fold) with Isoton II solution (5 mL) and the number of cells were counted by Coulter-Counter Z1 (Beckmann-Coulter Ltd.).

As a negative control group, HDMEC was cultured in the same manner, but in the absence of the test compound, as described above. As a positive control group, HDMEC was cultured in the same manner, but using a bFGF solution (0.1 µg/mL medium) instead of the test compound solution.

Results:

The promoting activity of each test compound on HDMEC-proliferation is depicted in the following Table 2 to 5. From these results, it is clear that each of the test compounds (0.1-1 µM) exhibited an equipotent promoting activity on HDMEC proliferation as bFGF (0.1 µg/mL medium).

TABLE 2

| Test groups | | Number of cells after 96 hours (cells) |
|---|---|---|
| Compound No. 3 in Table 1 | 0.1 µM | $1.31 \times 10^4$ |
| | 1.0 µM | $1.61 \times 10^4$ |
| Negative control | | $0.95 \times 10^4$ |
| Positive control | | $1.31 \times 10^4$ |

TABLE 3

| Test groups | | Number of cells after 96 hours (cells) |
|---|---|---|
| Compound No. 4* in Table 1 | 0.1 µM | $2.04 \times 10^4$ |
| | 1.0 µM | $2.50 \times 10^4$ |
| Compound No. 42* in Table 1 | 0.1 µM | $1.87 \times 10^4$ |
| | 1.0 µM | $2.25 \times 10^4$ |
| Compound No. 43* in Table 1 | 0.1 µM | $1.74 \times 10^4$ |
| | 1.0 µM | $2.10 \times 10^4$ |
| Compound No. 45* in Table 1 | 0.1 µM | $2.01 \times 10^4$ |
| | 1.0 µM | $2.14 \times 10^4$ |
| Compound No. 52* in Table 1 | 0.1 µM | $2.00 \times 10^4$ |
| | 1.0 µM | $2.04 \times 10^4$ |
| Negative control | | $1.65 \times 10^4$ |
| Positive control | | $1.81 \times 10^4$ |

*hydrochloride

TABLE 4

| Test groups | | Number of cells after 96 hours (cells) |
|---|---|---|
| Compound No. 48* in Table 1 | 0.1 µM | $1.97 \times 10^4$ |
| | 1.0 µM | $2.37 \times 10^4$ |
| Compound No. 50* in Table 1 | 0.1 µM | $1.78 \times 10^4$ |
| | 1.0 µM | $1.97 \times 10^4$ |
| Negative control | | $1.68 \times 10^4$ |
| positive control | | $1.95 \times 10^4$ |

*hydrochloride

TABLE 5

| Test groups | | Number of cells after 96 hours (cells) |
|---|---|---|
| Compound No. 24 in Table 1 | 0.1 µM | $2.13 \times 10^4$ |
| | 1.0 µM | $2.41 \times 10^4$ |
| Compound No. 46* in Table 1 | 0.1 µM | $2.16 \times 10^4$ |
| | 1.0 µM | $2.28 \times 10^4$ |
| Compound No. 53 in Table 1 | 0.1 µM | $1.98 \times 10^4$ |
| | 1.0 µM | $2.11 \times 10^4$ |
| Negative control | | $1.58 \times 10^4$ |
| Positive control | | $2.03 \times 10^4$ |

*hydrochloride

EXPERIMENT 2

Promoting Activity In Vivo of the Pyridine Compound on Wound Healing

Method:

Spontaneously diabetic male mice (C57BL/KsJ-db/db Jcl, age: 9 weeks, weight: 30-40 g; Nippon-Clair; 4 mice/group) were bled until their ages became 10 to 12 weeks old. Under anesthesia with pentobarbiturate, hair of the mice were shaved on their dorsum and wiped with ethanol. A circular full-thickness skin wound (2 cm$^2$) was prepared on the dorsum of mice. A test compound solution in physiologically saline (20 µL; 10 µg/wound) was administered dropwise onto the wound site and the wound site was covered by a film-dressing (Bioclusive, trademark registered by Johnson & Johnson Inc.). Until the wound healed completely, administration of the test compound, change of the film-dressing, cleaning of the wound site and measuring the wound area were carried out every two to four days. Meanwhile, a physiological saline solution (20 µL) instead of the test compound solution was administered to mice of the control group.

Results:

The results are shown in the following Table 6 to 8. From these results, it is clear that the duration giving complete healing of wound in the test compound-treated group was significantly shorter than that in the control group.

TABLE 6

| Test groups | Days to give complete wound healing (Mean ± SEM) | p value (vs. Control, unpaired t-test, two-tailed) |
|---|---|---|
| Test compound-treated group (Compound No. 3 in Table 1) | 19.50 ± 0.5000 | 0.0004 |
| Control | 59.50 ± 5.575 | — |

TABLE 7

| Test groups | Days to give complete wound healing (Mean ± SEM) | p value (vs. Control, unpaired t-test, two-tailed) |
|---|---|---|
| Test compound-treated group (Compound No. 4* in Table 1) | 20.75 ± 2.250 | <0.0001 |
| Test compound-treated group (Compound No. 39* in Table 1) | 25.25 ± 6.303 | 0.0063 |
| Test compound-treated group (Compound No. 5* in Table 1) | 27.25 ± 8.250 | 0.0255 |
| Control | 52.25 ± 1.887 | — |

*hydrochloride

TABLE 8

| Test groups | Days to give complete wound healing (Mean ± SEM) | p value (vs. Control, unpaired t-test, two-tailed) |
|---|---|---|
| Test compound-treated group (Compound No. 48* in Table 1) | 18.25 ± 1.031 | 0.0063 |
| Control | 49.00 ± 8.000 | — |

*hydrochloride

Industrial Applicability

The medicament for the treatment of skin lesion of the present invention has a potent promoting activity on dermal microvascular cell proliferation and can be thereby applicable to the treatment (e.g., promotion of healing) of skin lesions such as wounds (traumatic wound, post-surgical wound and the like), decubitus ulcer or chronic skin ulcers (thermal ulcer, vascular obstructive ulcer including leg ulcer, diabetic ulcer and the like).

The invention claimed is:

1. A method for treatment of skin lesions in a mammal, wherein the skin lesions are selected from the group consisting of acute or chronic wounds, decubitus ulcers (pressure ulcer), thermal ulcers, vascular obstructive ulcers, leg ulcers, diabetic ulcers, traumatic ulcers, and post-surgical ulcers, which comprises topically administering to the mammal in need of said treatment a therapeutically effective amount of a pyridine compound of the following formula [I-A]:

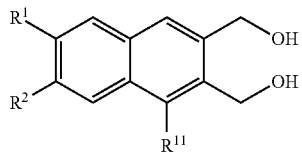

wherein $R^{11}$ is a group of the following formula:

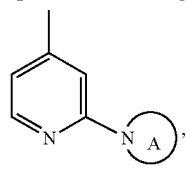

Ring A is a group of the following formula:

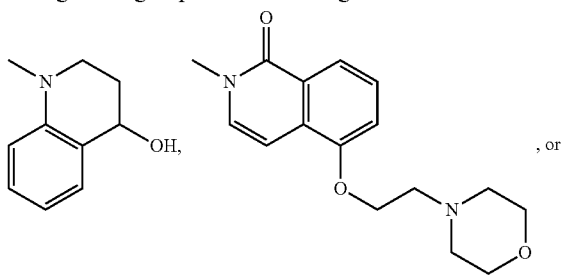, or

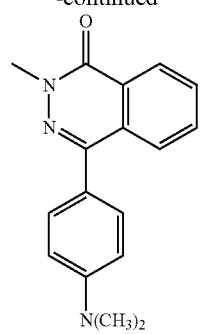

and $R^1$ and $R^2$ are the same or different and a $C_{1-6}$ alkoxy group; or a pharmaceutically acceptable salt of the pyridine compound, wherein the topical administration of the pyridine compound does not cause skin photosensitivity or cytotoxicity in the mammal.

2. The method according to claim 1, wherein the compound of formula [I-A] is selected from the group consisting of 2-(4-hydroxy-1,2,3,4-tetrahydroquinolin-1-yl)-4-[2,3-bis(hydroxymethyl)-6,7-dimethoxynaphthalen-1-yl]pyridine; and 4-[2,3-bis(hydroxymethyl)-6,7-dimethoxynaphthalen-1-yl]-2-[1-oxo-1,2-dihydro-5-(2-morpholinoethoxy)-soquinolin-2-yl]pyridine;

or a pharmaceutically acceptable salt thereof.

3. The method according to claim 1, wherein the compound of formula [I-A] is

1-[2-[4-[4-(N,N-dimethylamino)phenyl]-1(2H)-phtharadinon-2-yl]-4-pyridyl]-2,3-bis(hydroxymethyl)-6,7-dimethoxynaphthalene or a pharmaceutically acceptable salt thereof.

* * * * *

UNITED STATES PATENT AND TRADEMARK OFFICE
CERTIFICATE OF CORRECTION

PATENT NO.          : 8,809,360 B2                              Page 1 of 1
APPLICATION NO.     : 11/665807
DATED               : August 19, 2014
INVENTOR(S)         : Tamotsu Takagi et al.

It is certified that error appears in the above-identified patent and that said Letters Patent is hereby corrected as shown below:

In the Claims

*Claim 2, Col. 32, Lines 29-31,
"4-[2,3-bis(hydroxymethyl)-6,7-dimethoxynaphthalen-1-yl]-2-[1-oxo-1,2-dihydro-5-(2-morpholinoethoxy)-soquinolin-2-yl]pyridine;" should read as
--4-[2,3-bis(hydroxymethyl)-6,7-dimethoxynaphthalen-1-yl]-2-[1-oxo-1,2-dihydro-5-(2-morpholinoethoxy)-isoquinolin-2-yl]pyridine;--.

*Claim 3, Col. 32, Lines 36-40,
"1-[2-[4-[4-(N,N-dimethylamino)phenyl]-1(2H) -phtharadinon-2-yl]-4-pyridyl]-2,3-bis(hydroxymethyl)-6,7-dimethoxynaphthalene" should read as
--1-[2-[4-[4-(N,N-dimethylamino)phenyl]-1(2H)-phtharadinon-2-yl]-4-pyridyl]-2,3-bis(hydroxymethyl)-6,7-dimethoxynaphthalene--.

Signed and Sealed this
Twenty-fourth Day of March, 2015

Michelle K. Lee
*Director of the United States Patent and Trademark Office*